(12) United States Patent
Hirata et al.

(10) Patent No.: US 7,852,076 B2
(45) Date of Patent: *Dec. 14, 2010

(54) MAGNETIC RESONANCE APPARATUS UTILIZING TIME-VARYING RATE OF MAGNETIC RESONANT FREQUENCY

(75) Inventors: Satoshi Hirata, Kokubunji (JP); Hisaaki Ochi, Kodaira (JP); Yo Taniguchi, Kokubunji (JP); Tetsuhiko Takahashi, Soka (JP); Hiroyuki Takeuchi, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/423,431

(22) Filed: Apr. 14, 2009

(65) Prior Publication Data

US 2009/0201020 A1 Aug. 13, 2009

Related U.S. Application Data

(63) Continuation of application No. 10/562,643, filed on Dec. 28, 2005, now Pat. No. 7,518,362.

(30) Foreign Application Priority Data

Jun. 30, 2003 (JP) .............................. 2003-186099

(51) Int. Cl.
G01V 3/00 (2006.01)
(52) U.S. Cl. ........................................ 324/307; 324/314
(58) Field of Classification Search ................ 324/307, 324/314
See application file for complete search history.

(56) References Cited

U.S. PATENT DOCUMENTS

| 3,287,629 | A | 11/1966 | Varian |
| 3,501,688 | A | 3/1970 | Nelson |
| 4,689,566 | A | 8/1987 | Maudsley |
| 6,552,539 | B2 | 4/2003 | Uetake |

(Continued)

FOREIGN PATENT DOCUMENTS

JP 60-222043 11/1985

(Continued)

OTHER PUBLICATIONS

David G. Norris et al., "Fast Proton Spectroscopic Imaging Using the Sliced k-Space Method", MRM 30;641-645 (1993).

(Continued)

*Primary Examiner*—Louis M Arana
(74) *Attorney, Agent, or Firm*—Antonelli, Terry, Stout & Kraus, LLP.

(57) ABSTRACT

The present invention provides a magnetic resonance imaging system capable of performing spectrum measurement even when a magnetic resonant frequency changes during MRS measurement. A time-varying rate of a water magnetic resonant frequency is measured in advance before the MRS measurement. The amount of change in water magnetic resonant frequency during the MRS measurement is predicted from the measured time-varying rate. With the predicted value as the reference, a transmission frequency of an RF magnetic field irradiated in a signal suppression pulse sequence, a transmission frequency of an RF magnetic field for excitation and inversion and a received frequency at the detection of a magnetic resonance signal in a sequence of the MRS measurement are respectively set. A high-precision spectrum measurement is hence enabled.

1 Claim, 11 Drawing Sheets

U.S. PATENT DOCUMENTS

| | | |
|---|---|---|
| 7,042,215 B2 | 5/2006 | Moriguchi et al. |
| 7,215,119 B2 | 5/2007 | Kruger et al. |
| 7,233,143 B2 | 6/2007 | Moriguchi et al. |
| 7,355,405 B2 * | 4/2008 | Hirata et al. ............ 324/307 |
| 7,420,368 B2 * | 9/2008 | Miyazaki ............... 324/307 |
| 7,518,362 B2 * | 4/2009 | Hirata et al. ............ 324/307 |
| 2005/0033153 A1 | 2/2005 | Moriguchi et al. |
| 2005/0248343 A1 | 11/2005 | Kruger et al. |
| 2006/0255802 A1 | 11/2006 | Hirata et al. |
| 2007/0241754 A1 | 10/2007 | Hirata et al. |

FOREIGN PATENT DOCUMENTS

| | | |
|---|---|---|
| JP | 63-230156 | 9/1988 |
| JP | 63-292950 | 11/1988 |
| JP | 11-76191 | 3/1999 |
| JP | 2001-299720 | 10/2001 |
| JP | 2002-291718 | 10/2002 |
| JP | 2003-19124 | 1/2003 |

OTHER PUBLICATIONS

Joseph Granot et al., "Selected Volume Excitation Using Stimulated Echoes (VEST). Applications to Spatially Localized Spectroscopy and Imaging", Journal of Magnetic Resonance, 70, 488-492 (1986).

* cited by examiner

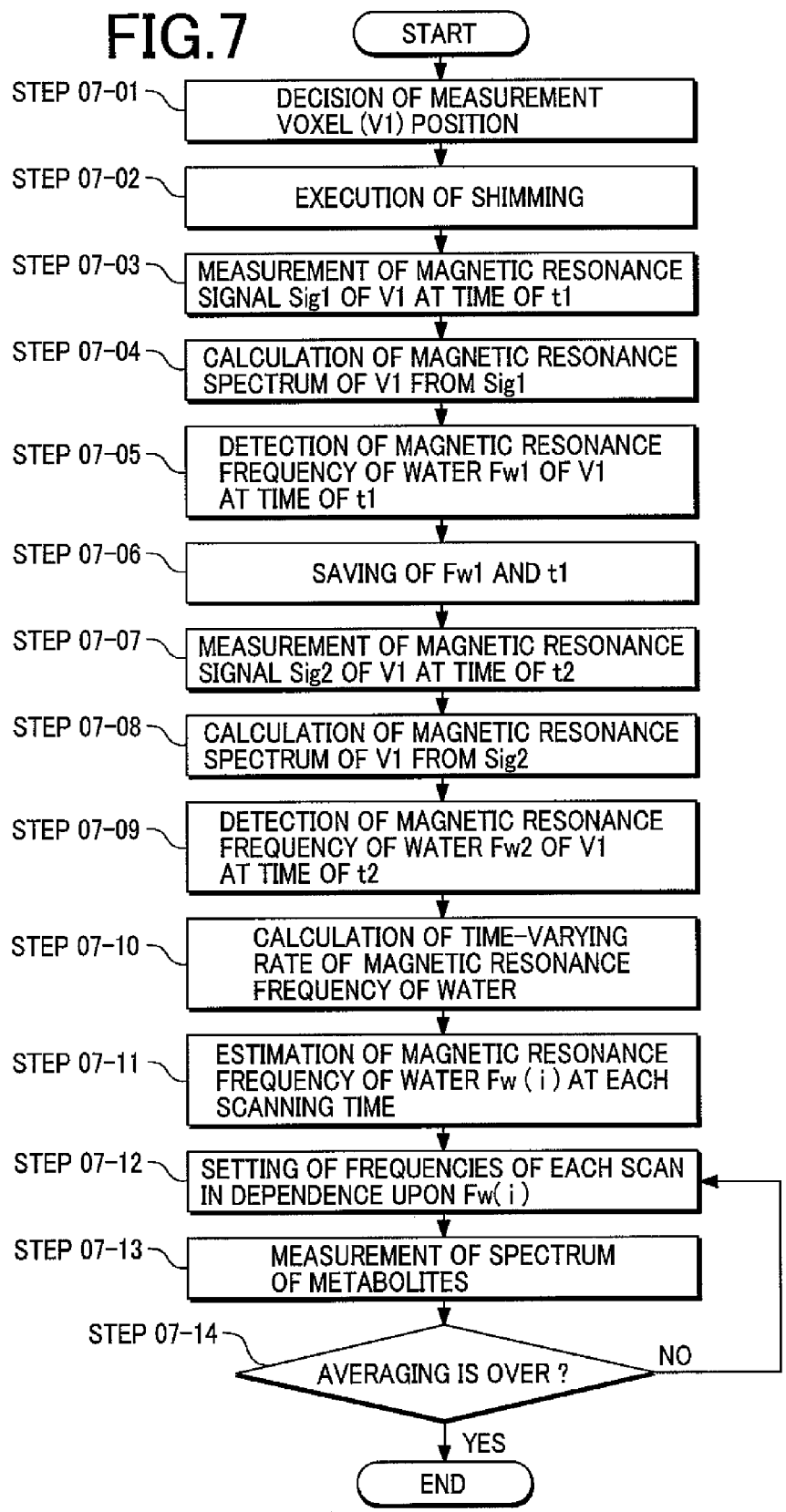

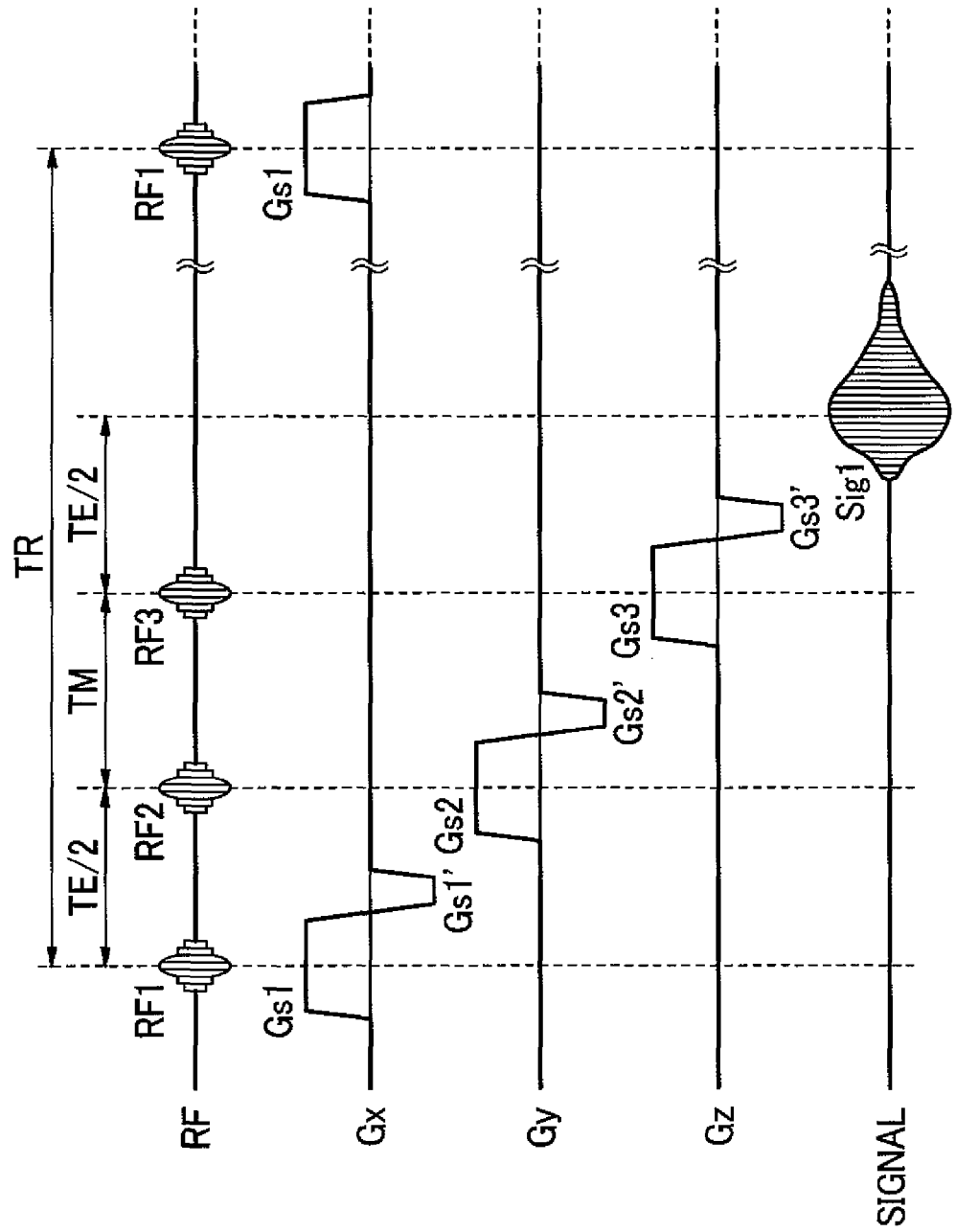

MAGNETIC RESONANCE APPARATUS UTILIZING TIME-VARYING RATE OF MAGNETIC RESONANT FREQUENCY

CROSS REFERENCE TO RELATED APPLICATION

This application is a Continuation of U.S. application Ser. No. 10/562,643, filed Dec. 28, 2005, now U.S. Pat. No. 7,518, 362 which claims priority from Japanese Patent Application No. 2003-186099, filed Jun. 30, 2003, the contents of which are incorporated herein by reference.

TECHNICAL FIELD

The present invention relates to a magnetic resonance imaging system, and particularly to a system suitable for measurement of a magnetic resonance signal including information about a chemical shift.

BACKGROUND ART

A magnetic resonance imaging system is capable of irradiating a target placed in a static magnetic field with an RF magnetic field of a specific frequency to excite nuclear magnetization of each proton contained in the target (magnetic resonance phenomenon), detecting a magnetic resonance signal generated from the target and thereby acquiring physical/chemical information. Widely-used Magnetic Resonance Imaging (hereinafter abbreviated as MRI) acquires images on which a density distribution of protons principally contained in a molecule of water in the target has been reflected.

As opposed to MRI, there is known a method called Magnetic Resonance Spectroscopy (hereinafter abbreviated as MRS) which separates magnetic resonance signals every molecules with a clue as to the difference (hereinafter called chemical shift) between magnetic resonant frequencies due to the difference between chemical bonds of various molecules containing protons (refer to e.g., J. Granot, "Selected Volume Excitation Using Stimulated Echo (VEST). Applications to Spatially Localized Spectroscopy and Imaging", J. Magn. Reson., vol. 70, pp. 488-492 (1986)).

A method for acquiring spectrums of a number of regions (pixels) simultaneously and performing imaging thereof every molecules is called Magnetic Resonance Spectroscopic Imaging (hereinafter abbreviated as MRSI). By using MRSI, a concentration distribution set every metabolites can visually be captured (refer to, for example, D. G. Norris, W. Dreher, "Fast Proton Spectroscopic Imaging Using the Sliced k-Space Method", Magn. Reson. Med., vol. 30, pp. 641-645 (1993)).

When a living body is intended for measurement, the concentration of each metabolite is often very low. Therefore, when a signal is measured without suppression of water of high concentration upon execution of MRS or MRSI measurement, a weak signal of a metabolite is buried in a skirt or base of an enormous signal peak generated from water, so it is very difficult to separate/extract a metabolite signal. Therefore, the prior art performs processing for suppressing a water signal immediately before execution of excitation and detection in accordance with an MRS or MRSI measurement sequence (refer to, for example, D. G. Norris, W. Dreher, "Fast Proton Spectroscopic Imaging Using the Sliced k-Space Method", Magn. Reson. Med., vol. 30. pp. 641-645 (1993)).

In the processing for suppressing the water signal, firstly, a transmission frequency is matched with a water peak position and an RF magnetic field in which an excitation frequency band width is narrowed to a water peak width or so is irradiated, in order to excite only nuclear magnetization contained in a water molecule. Next, the phases of nuclear magnetization contained in a number of water molecules each placed in an excitation state are rendered random and a dephase gradient magnetic field is applied to bring a vector sum of nuclear magnetization to zero (pseudo saturation). By performing excitation and detection in accordance with the MRS or MRSI measurement sequence while a pseudo saturation state of water magnetization is continuous, a weak metabolite signal was measured. Since the signal of each metabolite is very weak, a large number of averages are often performed to improve a signal-to-noise ratio (SNR) of each obtained spectrum in the conventional MRS or MRSI measurement.

As "a method for correcting a variation in magnetic resonant frequency with a change in static magnetic field strength" related to the present invention, there are known a report related to a method for performing the correction of a frequency variation in MRI (refer to, for example, Japanese Patent Application Laid-Open No. 2002-291718) and a report related to a method for performing the correction of a frequency variation in MRSI (refer to, for example, Japanese Patent Application Laid-Open No. Sho 63-230156).

DISCLOSURE OF THE INVENTION

In the conventional MRS measurement, a transmission frequency at the irradiation of an RF magnetic field and a received frequency at the detection of a magnetic resonance signal have been set assuming that a static magnetic field strength is constant in time. Described specifically, a spectrum measurement (pre-measurement for the detection of magnetic resonant frequency) is carried out at least once without suppressing a water signal before the MRS measurement to detect a magnetic resonant frequency of water. It is assumed that the static magnetic field strength is constant in time during an MRS measurement executed subsequently to the magnetic resonant frequency detecting pre-measurement (i.e., it is assumed that the magnetic resonant frequency is constant).

However, the static magnetic field strength might change during the MRS measurement depending upon the structure and characteristics of a magnet which generates a static magnetic field, and a measurement environment thereof. In such a case, the MRS measurement is accompanied by problems that with a shift in magnetic resonant frequency, even though the measurement is repeated for averaging, the rate of suppression of water is reduced gradually, an excitation slice position is displaced by degrees, and an SNR enhancing effect based on the averaging is not obtained.

The conventional MRS measurement is performed assuming that the magnetic resonant frequency is constant. No consideration was given to a variation in magnetic resonant frequency.

An object of the present invention is to provide a magnetic resonance imaging system which makes it possible to perform a high-precision spectrum measurement even when a magnetic resonant frequency changes during measurement.

In order to solve the above problems, a time-varying rate of a water magnetic resonant frequency is measured in advance before the MRS or MRSI measurement, and the amount of change in water magnetic resonant frequency at the MRS or MRSI measurement is predicted from the time-varying rate. With the predicted value as the reference, respective set values of a transmission frequency of an RF magnetic field irradiated in a water signal suppression pulse sequence, a transmission frequency of an RF magnetic field for excitation and inversion and a received frequency at the detection of a magnetic resonance signal in a sequence of the MRS or MRSI measurement are changed momentarily during measurement. Alternatively, a plurality of magnetic resonance signals measured in the sequence of the MRS or MRSI measurement are shifted according to a change in frequency (this frequency change is predicted on the basis of the time-varying rate of the pre-measured water magnetic resonant frequency) and added together.

Upon repeating the MRS or MRSI measurement for the purpose of averaging and phase-encoding, a measurement for detecting a water magnetic resonant frequency for each predetermined number of times is carried out. At a measurement subsequent to it, with the detected value as the reference, a transmission of an RF magnetic field irradiated in the water signal suppression pulse sequence, a transmission frequency of an RF magnetic field for excitation and inversion and a received frequency at the detection of a magnetic resonance signal in the sequence of the MRS or MRSI measurement are respectively set.

In the present invention, a time-varying rate of a water magnetic resonant frequency is measured in advance before an MRS or MRSI measurement, and the amount of change in water magnetic resonant frequency during the MRS or MRSI measurement is predicted from the measured time-varying rate. With the predicted value as the reference, a transmission frequency of an RF magnetic field irradiated in a water signal suppression pulse sequence, a transmission frequency of an RF magnetic field for excitation and inversion and a received frequency at the detection of a magnetic resonance signal in a sequence of the MRS or MRSI measurement are respectively set. As a result, a high-precision spectrum measurement is enabled even when the magnetic resonant frequency changes during the MRS or MRSI measurement.

A magnetic resonance imaging system of the present invention is provided with means which generates a static magnetic field, gradient magnetic field generating means which generates a gradient magnetic field, RF magnetic field generating means which generates an RF magnetic field, measuring means which measures a magnetic resonance signal generated from a target, computing means which performs a computation on the measured magnetic resonance signal, memory means which stores the measured magnetic resonance signal and the result of computation by the computing means, and sequence control means which sets operating conditions to respective portions of the gradient magnetic field generating means, the RF magnetic field generating means, the measuring means, the computing means and the memory means to control the operations of the respective portions.

In a first constitution, the sequence control means performs, when the measurement of a magnetic resonance signal is performed repeatedly plural times, control (1) to execute a pre-scan for measuring a magnetic resonant frequency of water each time the magnetic resonance signal is measured a predetermined number of times, (2) to detect a magnetic resonant frequency of water from a magnetic resonance spectrum obtained by Fourier-transforming the magnetic resonance signal obtained by the pre-scan, and (3) to set, based on the magnetic resonant frequency of water detected in (2), a transmission frequency of an RF magnetic field radiated into a target or/and a received frequency at the measurement of the magnetic resonance signal in a pulse sequence executed subsequently to the pre-scan.

In a second constitution, the sequence control means performs control (1) to execute a water suppression sequence for applying an RF magnetic field and a gradient magnetic field to a target to thereby suppress a signal of water, (2) to execute a spectrum measurement sequence for applying the RF magnetic field and the gradient magnetic field to the target to select and excite a predetermined voxel and measuring a magnetic resonance signal generated from the predetermined voxel, (3) to execute a pre-scan sequence for measuring a magnetic resonant frequency of water prior to (1) and (2) being executed a predetermined number of times, where (1) and (2) are performed repeatedly plural times, and (4) to, on the basis of the magnetic resonant frequency of water detected in (3), set a transmission frequency of the RF magnetic field irradiated in the water suppression sequence and set a transmission frequency of the RF magnetic field irradiated to select and excite the predetermined voxel or/and a received frequency at the detection of the magnetic resonance signal generated from the predetermined voxel in the spectrum measurement sequence.

In a third constitution, the sequence control means performs control (1) to execute a water suppression sequence for applying an RF magnetic field and a gradient magnetic field to a target to thereby suppress a signal of water, (2) to execute a spectrum measurement sequence for applying the RF magnetic field and the gradient magnetic field to the target to select and excite a predetermined voxel and measuring a magnetic resonance signal generated from the predetermined voxel, (3) to, when (1) and (2) are performed repeatedly plural times, detect a water signal peak from a magnetic resonance spectrum obtained by Fourier-transforming the magnetic resonance signal obtained by the execution of (1) and (2), each time (1) and (2) are executed a predetermined number of times to calculate a signal strength of the water signal peak, (4) to determine that a water magnetic resonant frequency has been shifted when the calculated signal strength of water signal peak is increased to a predetermined value or more, (5) to execute a pre-scan for measuring the water magnetic resonant frequency when the water magnetic resonant frequency is judged to have been shifted in (4), (6) to detect a magnetic resonant frequency of water from a magnetic resonance spectrum obtained by Fourier-transforming the magnetic resonance signal obtained in the pre-scan, and (7) to, on the basis of the magnetic resonant frequency of water detected in (6), set, in a pulse sequence executed subsequently to the pre-scan, a transmission frequency of the RF magnetic field irradiated in the water suppression sequence, or/and set a transmission frequency of the RF magnetic field irradiated to select and excite the predetermined voxel in the spectrum measurement sequence, or/and set a received frequency at the detection of the magnetic resonance signal generated from the predetermined voxel.

According to the above-described first, second and third constitutions, a position displacement and a shift in position information can be reduced by performing a frequency correction even when the magnetic resonant frequency changes during measurement. Also, a high-precision spectrum measurement is enabled.

In the following constitution, the sequence control means includes control to irradiate a target with an RF magnetic field at least once, measure a magnetic resonance signal generated after the irradiation of the RF magnetic field in a state in which the strength of application of a gradient magnetic field is approximately zero, and calculate magnetic resonance spectrum information from the measured magnetic resonance signal to thereby perform a magnetic resonance spectrum measurement.

In a fourth constitution, the sequence control means performs control (1) to measure a first magnetic resonance signal generated from a measurement voxel at a magnetic resonance spectrum measurement at a first time interval, (2) to detect a magnetic resonant frequency F1 of water from a first magnetic resonance spectrum obtained by Fourier-transforming the first magnetic resonance signal, (3) to measure a second magnetic resonance signal generated from the voxel at a second time interval subsequent to the elapse of a predetermined time from the measurement of the first magnetic resonance signal, (4) to detect a magnetic resonant frequency F2 of water from a second magnetic resonance spectrum obtained by Fourier-transforming the second magnetic resonance signal, and (5) to calculate a time-varying rate of the magnetic resonant frequency of water on the basis of the F1 and F2.

In a fifth constitution, the sequence control means performs control (1) to measure a first magnetic resonance signal generated from a measurement voxel at a magnetic resonance spectrum measurement at a first time interval, (2) to detect a magnetic resonant frequency F1 of water from a first magnetic resonance spectrum obtained by Fourier-transforming the first magnetic resonance signal, (3) to measure a second magnetic resonance signal generated from the voxel at a second time interval subsequent to the elapse of a predetermined time from the measurement of the first magnetic resonance signal, (4) to detect a magnetic resonant frequency F2 of water from a second magnetic resonance spectrum obtained by Fourier-transforming the second magnetic resonance signal, (5) to estimate, based on the F1 and F2, a time-varying rate of a magnetic resonant frequency of water at a measurement time at which the magnetic resonance signal is measured after the completion of measurement of the second magnetic resonance signal, (6) to calculate, using the estimated time-varying rate of the magnetic resonant frequency, a transmission frequency of an RF magnetic field or/and a received frequency at which the magnetic resonance signal generated from the voxel is received and measure the magnetic resonance signal generated from the voxel after the setting of the operating conditions of the RF magnetic field generating means or/and the measuring means, and (7) to perform (6) repeatedly plural times subsequently to the completion of measurement of the second magnetic resonance signal.

In a sixth constitution, the sequence control means performs, when the measurement of a magnetic resonance signal is performed repeatedly plural times, control (1) to execute a pre-scan for measuring a magnetic resonant frequency of water each time the magnetic resonance signal is measured a predetermined number of times, (2) to detect a magnetic resonant frequency of water from a magnetic resonance spectrum obtained by Fourier-transforming the magnetic resonance signal obtained by the pre-scan, and (3) to set, based on the magnetic resonant frequency detected in (2), a transmission frequency of an RF magnetic field radiated into a target or/and a received frequency at the measurement of the magnetic resonance signal in a spectrum measurement sequence executed subsequently to the pre-scan.

According to the above-described fourth, fifth and sixth constitutions, a high-precision spectrum measurement is enabled even when the magnetic resonant frequency changes during measurement.

BRIEF DESCRIPTION OF THE DRAWINGS

FIG. 7 is a flowchart depicting a procedure for MRS measurement in an embodiment 1 of the present invention;

FIG. 11 is a view showing one example of a pulse sequence for MRS measurement, which is applicable to the embodiment of the present invention.

BEST MODE FOR CARRYING OUT THE INVENTION

Figure 1A:
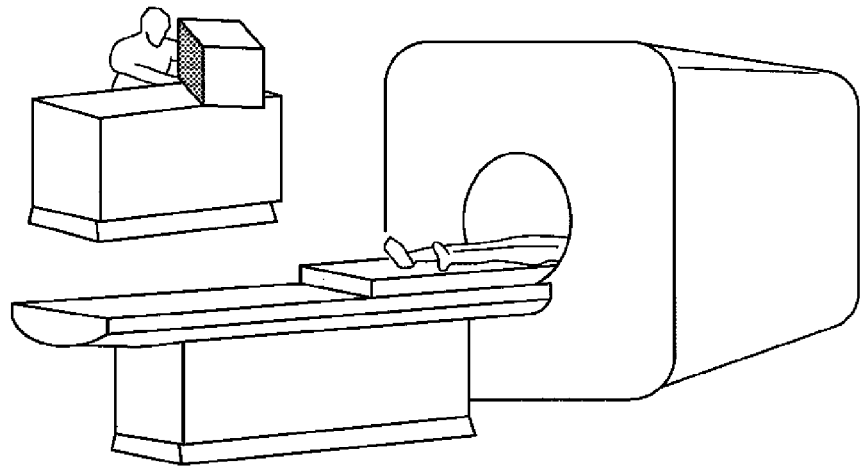
FIGS. 1A to 1C are external views illustrative of magnetic resonance imaging systems to which the present invention is applied.
Figure 1B:
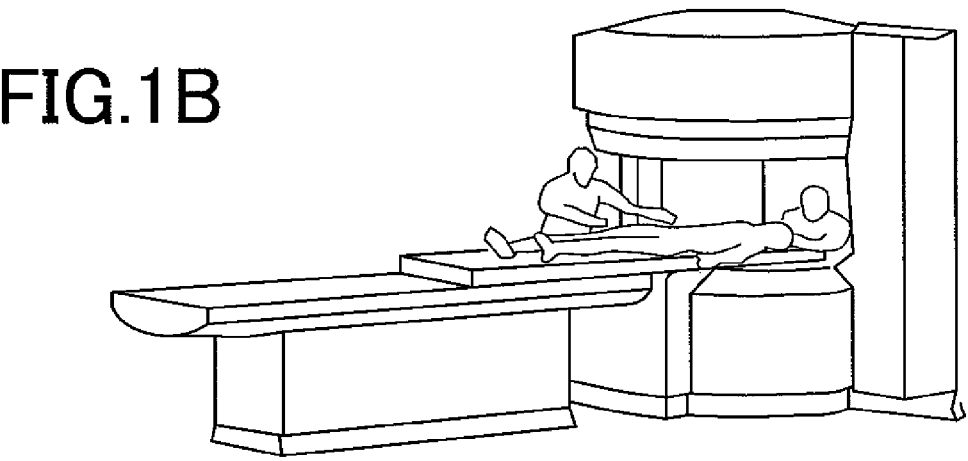
Figure 1C:
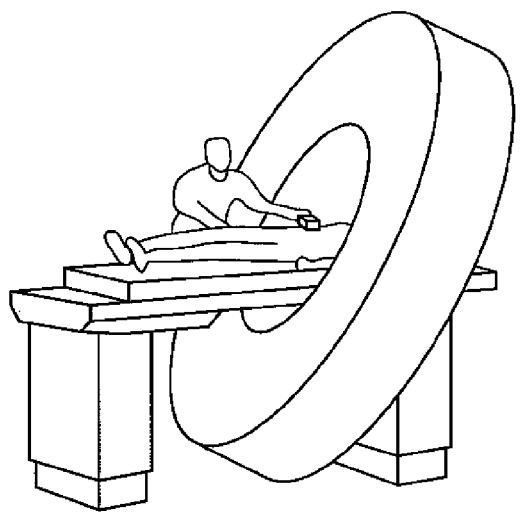

FIG. 1 is an external view illustrative of magnetic resonance imaging systems to which the present invention is applied. FIG. 1A is a magnetic resonance imaging system which makes use of a tunnel type magnet which generates a static magnetic field through a solenoid coil, and FIG. 1B is a hamburger type magnetic resonance imaging system in which magnets are separated into upper and lower sections to enhance a sense of openness. FIG. 1C is a magnetic resonance imaging system of the same tunnel type as FIG. 1A. In the magnetic resonance imaging system, however, a magnet is made short in depth and aslant inclined to thereby enhance a sense of openness.

Figure 2:
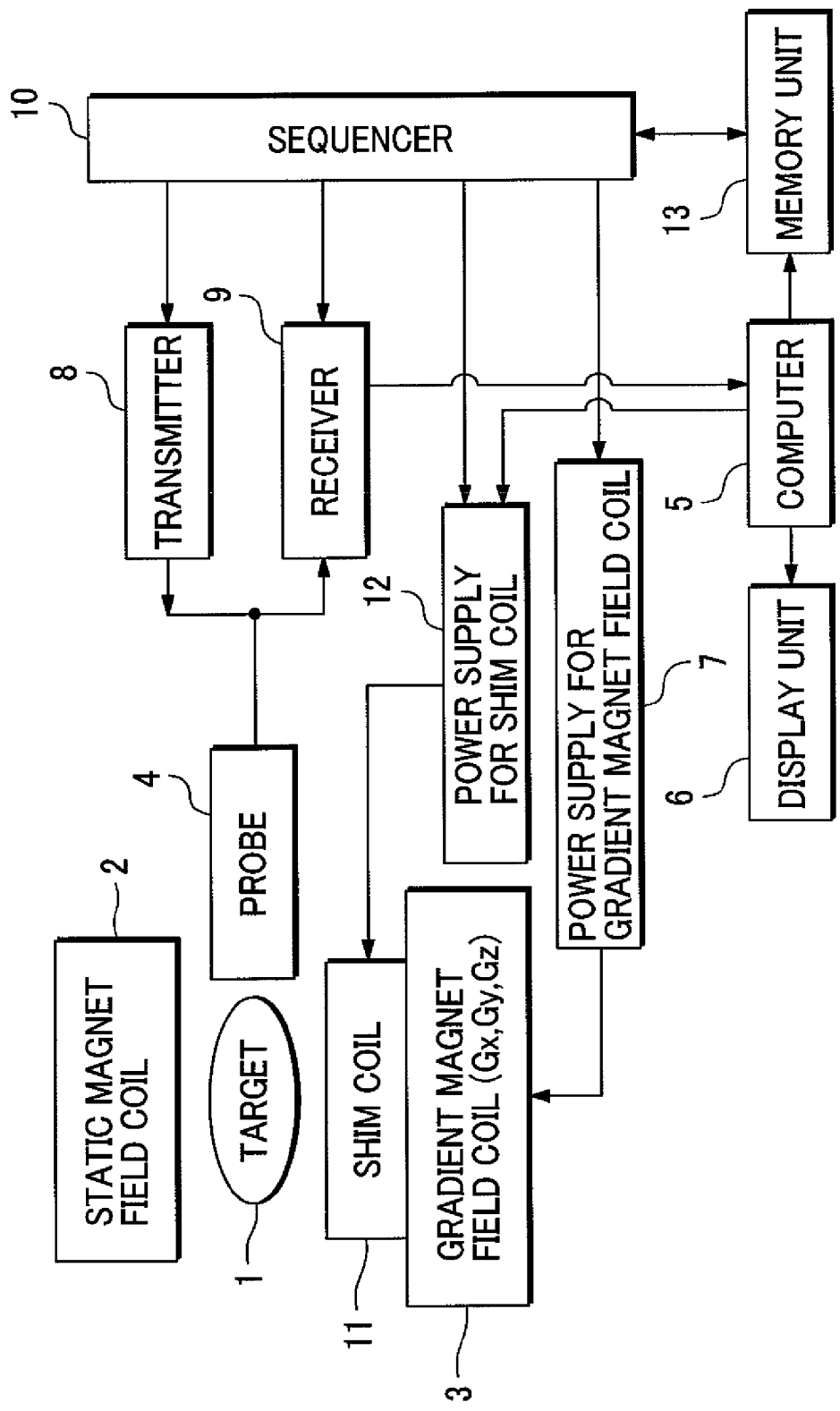
FIG. 2 is a view showing a construction example of a magnetic resonance imaging system to which the present invention is applied.

FIG. 2 is a view showing an example of construction of a magnetic resonance imaging system to which the present invention is applied. A target 1 is placed in space to which a static magnetic field generated by a static magnetic field generating magnet 2 and three-direction gradient magnetic fields orthogonal to one another generated by a gradient magnetic field generating coil 3 are applied. A shim coil 11 might be provided which is capable of adjusting the uniformity of a static magnetic field by changing a current caused to flow through each coil. An RF magnetic field produced by a probe 4 is applied to the subject 1 to generate a magnetic resonance phenomenon. A magnetic resonance signal generated from the subject 1 is detected by the probe 4. Incidentally, the applied RF magnetic field is generated by a transmitter 8 and the detected magnetic resonance signal is transmitted to a computer 5 through a receiver 9. The computer 5 performs various computing processes on the magnetic resonance signal to generate spectrum information and image information, and displays these information on a display 6 and records them in a memory unit 13 (measurement conditions or the like are also recorded in the memory unit 13 as needed). A power supply 12 for the shim coil 11, a power supply 7 for the gradient magnetic field generating coil 3, the transmitter 8 and the receiver 9 are controlled by a sequence controller 10. Incidentally, FIG. 2 shows an example in which the probe 4 is used for sharing of transmission/reception. However, a probe for transmission and a probe for reception might be provided separately from each other.

A pulse sequence used in an embodiment of the present invention will be explained below.

Figure 3:
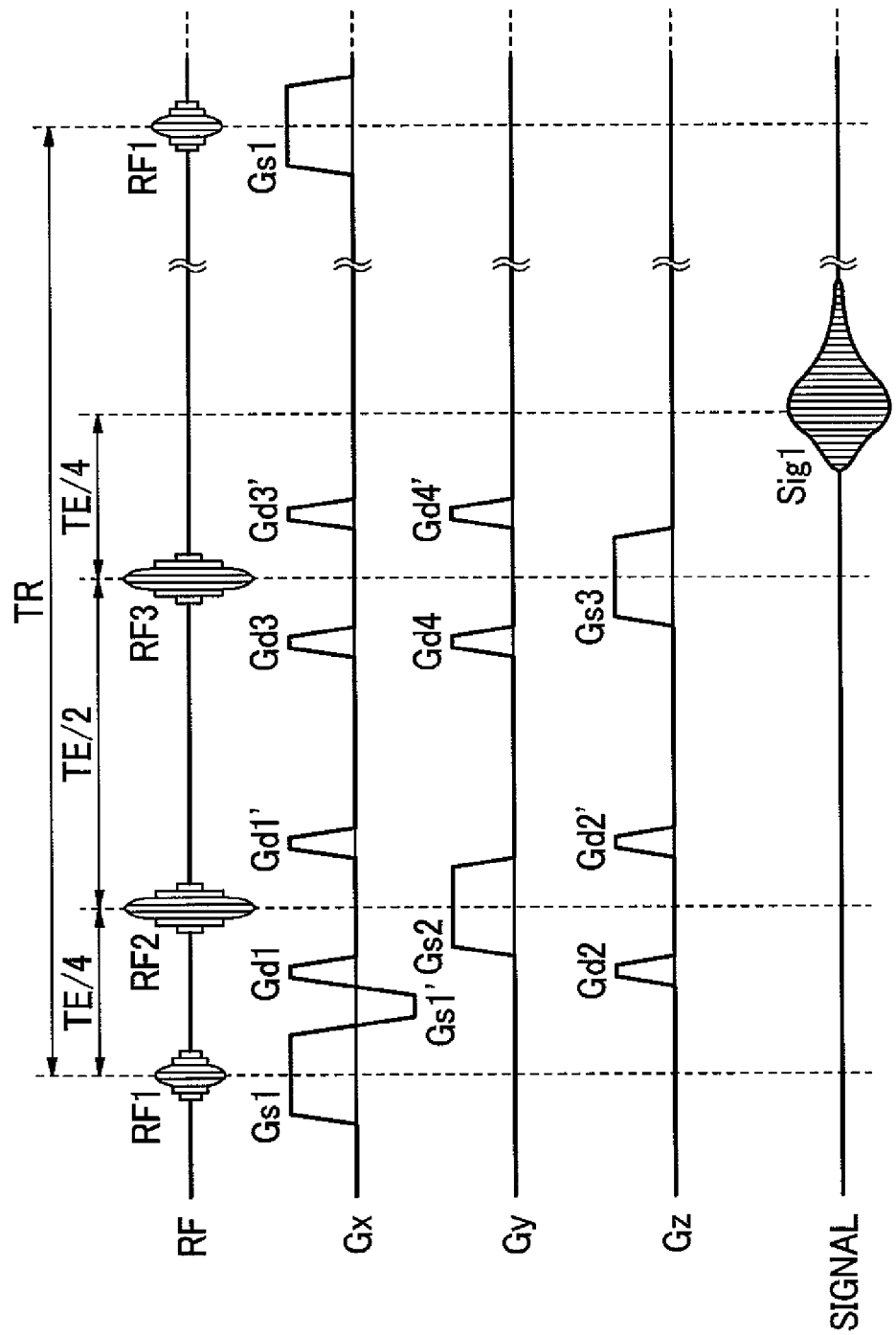
FIG. 3 is a view illustrating one example of an MRS pulse sequence used in an embodiment of the present invention.

FIG. 3 is a view showing one example of a pulse sequence (MRS pulse sequence) for MRS measurement, which is used in the embodiment of the present invention. In the MRS pulse sequence shown in FIG. 3, a first gradient magnetic field (gradient magnetic field in an X-axis direction) Gs1 for selection of a first slice (plane vertical to an X axis), and a first RF magnetic field RF1 called "90° pulse" are first applied simultaneously to enable nuclear magnetization in the first slice to be brought into an excitation state. Here, TE is assumed to be an echo time, and TR is assumed to be a repetition time.

Next, a second gradient magnetic field (gradient magnetic field in a Y-axis direction) Gs2 for selection of a second slice (plane orthogonal to a Y axis), and a second RF magnetic field RF2 called "180° pulse" are simultaneously applied after the elapse of TE/4 from the irradiation of RF1 to allow nuclear magnetization contained even in the second slice, of the nuclear magnetization in the first slice, which has been excited by RF1 to be 180° reversed.

Further, after the elapse of TE/2 from the irradiation of RF2, a third gradient magnetic field (gradient magnetic field in a Z-axis direction) Gs3 for selection of a third slice (plane vertical to a Z axis), and a third RF magnetic field RF3 called "180° pulse" are simultaneously applied to enable nuclear magnetization contained even in the third slice, of the nuclear magnetization lying in an intersection area of the first slice and the second slice reversed by RF2 to be 180° reversed again. With the application of the above three sets of RF magnetic fields and gradient magnetic fields, a magnetic resonance echo signal Sig1 with the point of time subsequent to TE/4 from the irradiation of RF3 as an echo time can be generated.

Incidentally, Gs1' applied immediately after the application of Gs1 is a gradient magnetic field for rephase with respect to Gs1. Gd1 and Gd1', and Gd2 and Gs2' applied before and after the application of RF2 are respectively gradient magnetic fields for dephasing the nuclear magnetization excited by the irradiation of RF2 without disturbing the phase of the nuclear magnetization excited by the irradiation of RF1 (a change in phase being canceled by Gd1 and Gd1' and a change in phase being canceled by Gd2 and Gd2'). Further, Gd3 and Gd3', and Gd4 and Gd4' applied before and after the application of RF3 are respectively gradient magnetic fields for dephasing the nuclear magnetization excited by the irradiation of RF3 without disturbing the phase of the nuclear magnetization excited by the irradiation of RF1 (a change in phase being canceled by Gd3 and Gd3' and a change in phase being canceled by Gd4 and Gd4').

With the execution of the pulse sequence shown in FIG. 3, it is possible to selectively excite only the nuclear magnetization contained in an area (imaging voxel) V1 where the above three slices intersect. And the magnetic resonance signal generated from the imaging voxel V1 is measured and Fourier transform is effected on the measured magnetic resonance signal, whereby a magnetic resonance spectrum of the imaging voxel V1 can be obtained.

There are often cases in which a SINC waveform (sin(t)/t) having a rectangular excitation frequency characteristic is normally used in each of the first RF magnetic field RF1 and the second RF magnetic field RF2.

When MRS measurement is carried out without suppressing a signal of water upon execution of the MRS measurement, a weak signal of a metabolite is buried in the skirt or base of an enormous signal peak generated from water. It is thus very difficult to separate and extract the metabolite signal. Therefore, upon the MRS measurement at the time that the metabolite signal is detected, a process for suppressing the water signal is carried out immediately before excitation/detection by the sequence of FIG. 3.

Figure 4:
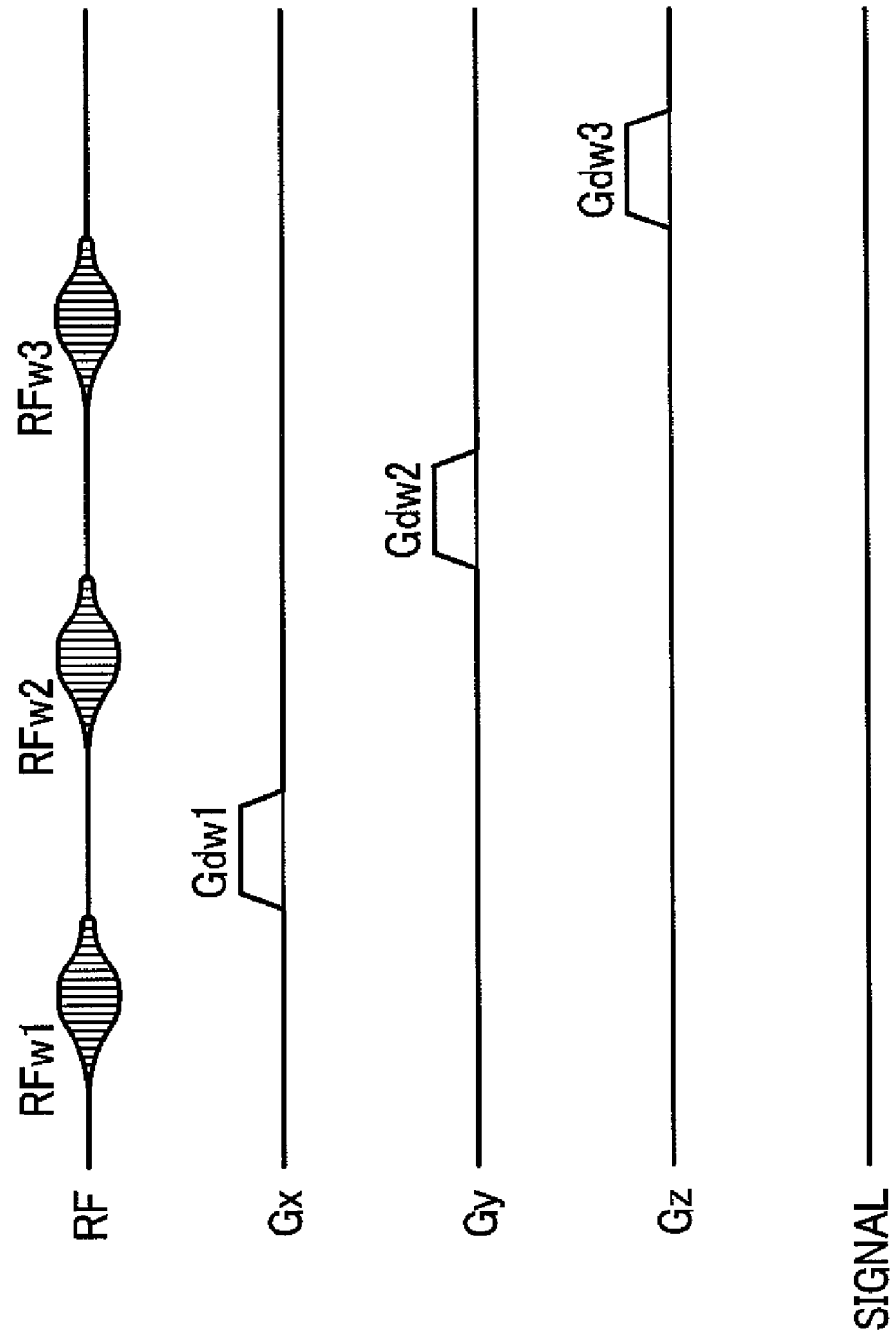
FIG. 4 is a view depicting one example of a pulse sequence for suppressing a water signal, which is used in the embodiment of the present invention.

FIG. 4 is a view showing one example of a pulse sequence (water signal suppression pulse sequence) for suppressing the wafer signal, which is used in the embodiment of the present invention. It is the water signal suppression method described in the non-patent document 2. In the pulse sequence shown in FIG. 4, an RF magnetic field (RF magnetic field for water excitation) RFw1 in which a transmission frequency Ft is set to a magnetic resonant frequency Fw of water and an excitation frequency band width ΔFt is set to a wafer peak width ΔFw or so, is first irradiated to excite only nuclear magnetization contained in molecules of water (selective excitation of water magnetization).

Next, a dephase gradient magnetic field Gdw1 is applied to put as under the phases of nuclear magnetization contained in the water molecules placed in the excitation state and bring a vector sum of water's magnetization to zero (pseudo saturation of water magnetization).

In order to further increase the effect of suppressing the water signal, the application of an RF magnetic field and a dephase gradient magnetic field similar to the RF magnetic field RFw1 for water excitation and the dephase gradient magnetic field Gdw1 is often performed repeatedly three times or so (FIG. 4 shows a sequence example in which the application is repeated three times).

Incidentally, a Gauss waveform having an excitation frequency characteristic of a narrow bandwidth is often used as the RF magnetic field RFw1. Although the example shown in FIG. 4 is of an example in which a gradient magnetic field of any one axis of Gx, Gy and Gz is applied as the dephase gradient magnetic field, gradient magnetic fields of all three axes of Gx, Gy and Gz may be applied simultaneously. Alternatively, any two axes may be applied simultaneously.

A weak signal of a metabolite can be measured by performing excitation/detection in accordance with the sequence of FIG. 3 while the pseudo saturation state of the water magnetization is continuing.

Incidentally, while the flip angle of the RF magnetic field RFw for water excitation is normally often set to the neighborhood of 90°, various combinations or numerical values are used as the applied number of axes or applying strengths as to the dephase gradient magnetic fields Gdw. Since a signal of a metabolite detectable from within a living organism is normally often very weak, a number of averages are often performed for the purpose of enhancing a signal-to-noise ratio (SNR) of an obtainable spectrum.

Figure 5:
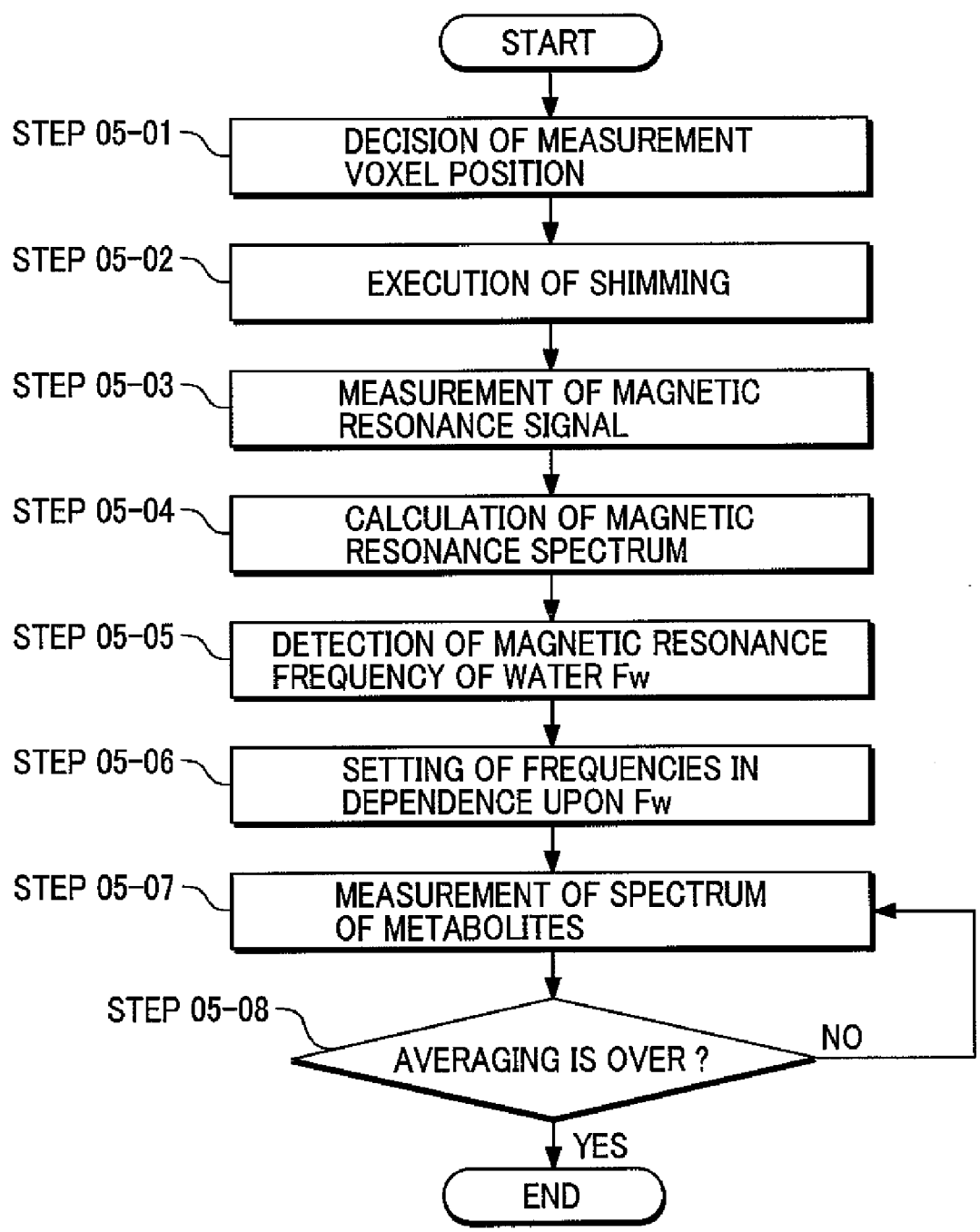
FIG. 5 is a flowchart showing a procedure for MRS measurement assuming that a static magnetic field strength is constant in time in the embodiment of the present invention.

FIG. 5 is a flowchart showing an MRS measurement procedure where assuming that a static magnetic field strength is constant in time (magnetic resonant frequency is constant), a transmission frequency at the irradiation of an RF magnetic field and a received frequency at the detection of a magnetic resonance signal are set once alone in the embodiment of the present invention. A summary of an imaging or measuring procedure will be explained below.

STEP05-01: An imaging voxel V1 of a target is determined.

STEP05-02: Shimming for enhancing the uniformity of a static magnetic field is performed if necessary.

STEP05-03: A magnetic resonance signal Sig generated from a predetermined area containing the imaging voxel V1 is acquired using the MRS sequence.

STEP05-04: Fourier transform is effected on the acquired magnetic resonance signal to calculate a magnetic resonance spectrum.

STEP05-05: A water magnetic resonant frequency Fw is detected from the magnetic resonance spectrum.

STEP05-06: With the value of the detected Fw as the reference, the respective values of a transmission frequency of an RF magnetic field irradiated in accordance with the process of suppressing a water signal, a transmission frequency of an RF magnetic field irradiated to selectively excite the imaging voxel V1, and a received frequency at the detection of the magnetic resonance signal generated from the imaging voxel V1 are set.

STEP05-07: The water signal suppression pulse sequence shown in FIG. 4 and the MRS sequence shown in FIG. 3 are continuously performed to measure a spectrum of each metabolite.

STEP05-08: STEP05-07 is repeated as needed to perform a signal averaging.

In the imaging procedure shown in FIG. 5, the transmission frequency at the irradiation of the RF magnetic field and the received frequency at the detection of the magnetic resonance signal are set once alone assuming that the static magnetic field strength is constant in time. Therefore, when the static magnetic field strength changes in time due to some causes, the position of a measured voxel is shifted, the position of a measured peak is shifted so that a sufficient averaging effect is not obtained, and the suppression of the water signal becomes insufficient, as the number of averages increases.

Figure 6A:
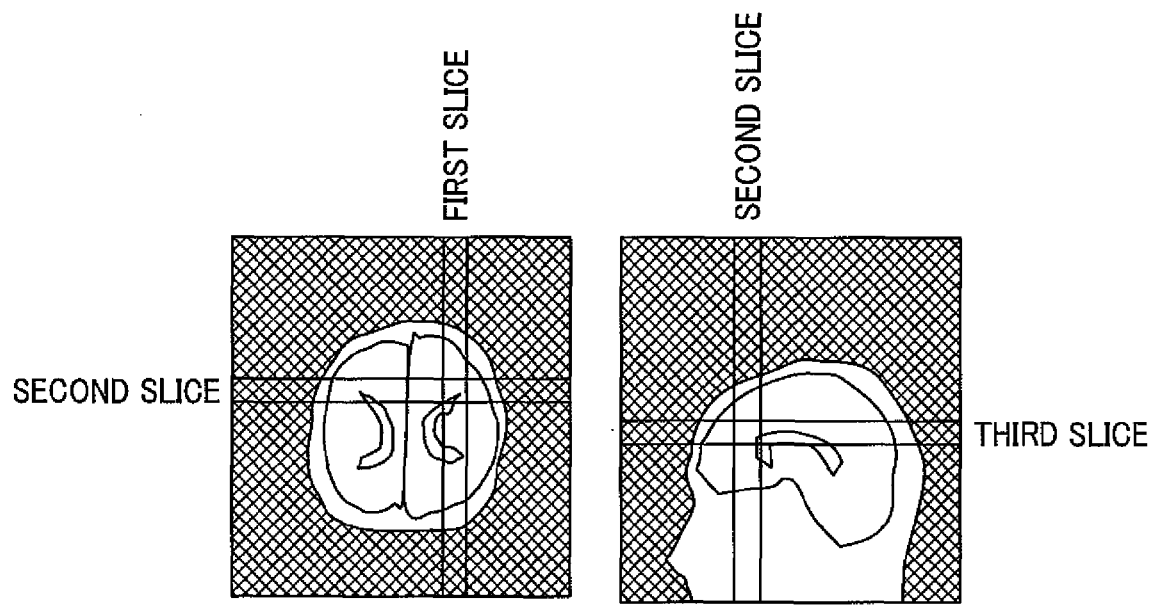
FIG. 6A is a view illustrating the manner of positioning of imaging voxels at the flowchart of FIG. 5.
Figure 6B:
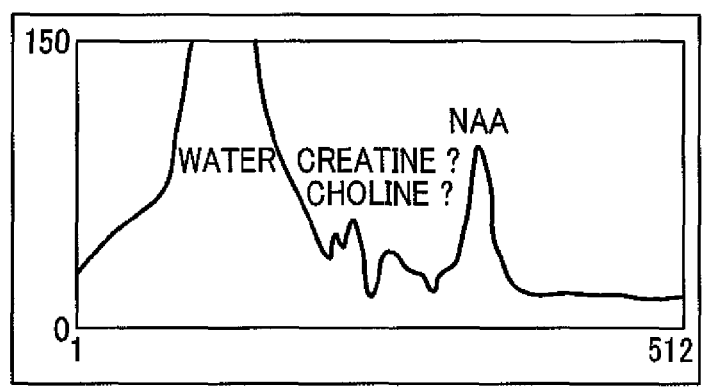
FIG. 6B is a view showing an example of a measurement result of MRS, which is measured in accordance with the flowchart of FIG. 5 where a static magnetic field strength changes with time.

FIG. 6 is a measurement result example at the time that the measurement is carried out in accordance with the procedure of FIG. 5 where the static magnetic field strength changes in time. FIG. 6A shows the manner in which in the procedure shown in FIG. 5 for determining the position of the imaging voxel, the positions of three slices (first slice, second slice and third slice) orthogonal to one another on a magnetic resonance image are adjusted to thereby determine the corresponding imaging voxel position. FIG. 6B shows a spectrum obtained from the imaging voxel. In FIG. 6B, the peaks of choline and creatine, which should originally be separable and observable, are superimposed on each other and buried in the skirt or base of a water signal whose suppression is insufficient. A half-value width of a peak of NAA is also made wide.

Embodiment 1

The embodiment 1 will propose a method for, when an MRS measurement with repetitive measurements of plural times is executed, performing a pre-scan for measuring a time-varying rate of each water magnetic resonant frequency in advance before the execution of the MRS measurement, predicting the amount of change in MRS-measured water magnetic resonant frequency from the time-varying rate of each water magnetic resonant frequency, and setting, with the predicted value as the reference, a transmission frequency of an RF magnetic field irradiated in accordance with a water signal suppression pulse sequence, a transmission frequency of an RF magnetic field for excitation and inversion in an MRS sequence, and a received frequency at the detection of a magnetic resonance signal.

FIG. 7 is a flowchart showing a procedure for the MRS measurement, which is employed in the embodiment 1 of the present invention. A specific imaging procedure will be explained below.

STEP07-01: An imaging voxel V1 of a target is determined.

STEP07-02: Shimming for enhancing the uniformity of a static magnetic field is performed if needed.

Incidentally, STEP07-01 and STEP07-02 may be executed by altering the sequence thereof.

STEP07-03: A first magnetic resonance signal Sig1 generated from the imaging voxel V1 is acquired at a first time t1 using the MRS pulse sequence shown in FIG. 3.

STEP07-04: Fourier transform is effected on Sig1 to calculate a first magnetic resonance spectrum.

STEP07-05: A water magnetic resonant frequency Fw1 is detected from the first magnetic resonance spectrum.

STEP07-06: t1 and Fw1 are saved in association with each other.

STEP07-07: A second magnetic resonance signal Sig2 generated from the imaging voxel V1 is acquired at a second time t2 subsequent to the elapse of a predetermined time from the time t1.

STEP07-08: Fourier transform is effected on Sig2 to calculate a second magnetic resonance spectrum.

STEP07-09: A water magnetic resonant frequency Fw2 is detected from the second magnetic resonance spectrum.

STEP07-10: A time-varying rate $(Fw2-Fw1)/(t2-t1)$ with respect to the water magnetic resonant frequencies can be calculated from the saved t1 and Fw1 and t2 and Fw2.

STEP07-11: When a magnetic resonance signal measurement (corresponding to such a measurement that the pulse sequence shown in FIG. 4, for suppressing the water signal and the MRS pulse sequence shown in FIG. 3 are continuously repeated N times) accompanied with N-time repetitive measurements is executed after the time t2, an estimated value Fw(i) of a water magnetic resonant frequency at each scanning or measurement time t(i) with respect to each of respective measurements Mi (where i=1, 2, 3, ..., N) of N times is calculated in accordance with an equation (1):

$$Fw(i)=Fw1+(Fw2-Fw1)/(t2-t1)\times(t(i)-t1) \quad (1)$$

STEP07-12: On the basis of the estimated value (amount of change in) of the water magnetic resonant frequency, set values of a transmission frequency Fwt(i) of an RF magnetic field irradiated to suppress a water signal set by each measurement Mi, a transmission frequency Ft(i) of an RF magnetic field irradiated to selectively excite and invert the imaging voxel V1, and a received frequency Fr(i) at the detection of a magnetic resonance signal generated from the imaging voxel V1 are respectively calculated in accordance with the following equations (2), (3) and (4):

$$Fwt(i)=Fw(i) \quad (2)$$

$$Ft(i)=Ft(i)+(Fw2-Fw1)/(t2-t1)\times(t(i)-t(1)) \quad (3)$$

$$Fr(i)=Fr(1)+(Fw2-Fw1)/(t2-t1)\times(t(i)-t(1)) \quad (4)$$

STEP07-13: Spectrums of metabolites are measured by continuously performing the sequences shown in FIGS. 4 and 3 using the calculated set values (Fwt(i), Ft(i) and Fr(i)).

STEP07-14: Signal averaging is performed by repeating STEP07-13 while the respective set values (Fwt(i), Ft(i) and Fr(i)) are being changed to the values calculated as above.

With the execution of the MRS measurement in accordance with the procedure of FIG. 7, a high-precision MRS measurement is enabled even in circumstances when a change in magnetic resonant frequency with a variation in magnetic field during measurement exists.

Figure 8A:
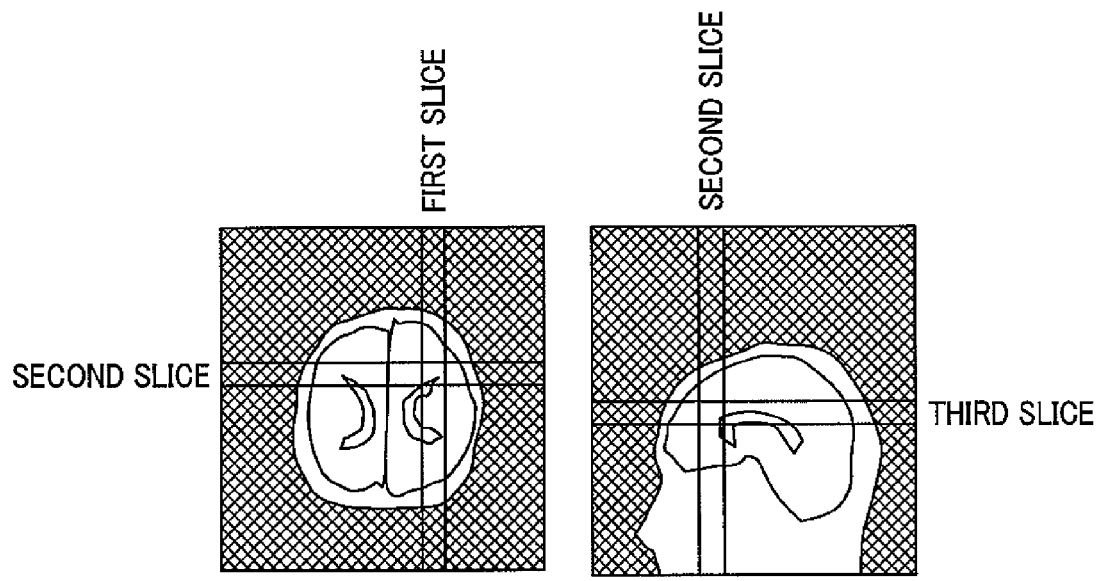
FIG. 8A is a view showing the positions of imaging voxels.
Figure 8B:
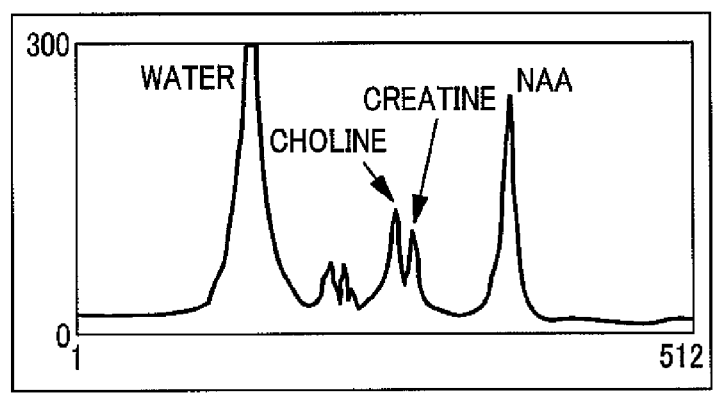
FIG. 8B is a view illustrating an example of a measurement result of MRS, which is measured in accordance with the flowchart of FIG. 7 where a static magnetic field strength changes with time.

FIG. 8 is a measurement result example at the time that the measurement is conducted in accordance with the procedure of FIG. 7 where a static magnetic field strength changes in time. FIG. 8A shows the positions of imaging voxels determined on magnetic resonance images by a first slice, a second slice and a third slice, and FIG. 8B shows a spectrum obtained from the imaging voxels. In FIG. 8B as compared with FIG. 6B, a water signal is sufficiently suppressed and a half-value width of a peak of NAA is also made narrow. The peaks of choline and creatine can also be separated.

Although the above example has described the case in which the water magnetic resonant frequencies at the given two times are measured to calculate the time-varying rate with respect to the water magnetic resonant frequencies, a higher precision time-varying rate with respect to water magnetic resonant frequencies can be calculated by minimum square fitting where the water magnetic resonant frequencies at three or more times are measured to calculate the time-varying rate.

Although the above example has explained the case in which assuming that the time-varying rate of each water magnetic resonant frequency has a linear change, the above-mentioned time-varying rate (Fw2−Fw1)/(t2−t1) is calculated, a high-order approximate characteristic is calculated by using the minimum square fitting or the like even where it has a change other than the linear change, whereby a change in water magnetic resonant frequency can be predicted.

A precision enhancing effect is obtained when time continuity exists in the varying rate of each water magnetic resonant frequency, whereas when no time continuity exists in the varying rate of the water magnetic resonant frequency as in the case where each water magnetic resonant frequency changes instantaneously, a sufficient precision enhancing effect might not be obtained. A description will be made below, of an embodiment 2 in which a sufficient precision enhancing effect can be expected even when no time continuity exists in the varying rate of each water magnetic resonant frequency.

Embodiment 2

The embodiment 2 will propose a method for, when such an MRS measurement with repetitive measurements of plural times that the pulse sequence shown in FIG. 4, for suppressing the water signal and the MRS pulse sequence shown in FIG. 3 are performed on a consecutive basis, is executed, pre-scanning a magnetic resonance signal for detecting a water magnetic resonant frequency for each predetermined number of repetitions during the execution of repetitive measurements, calculating water magnetic resonant frequencies for repetitive measurements conducted subsequently to the pre-scan, and setting, with each calculated value as the reference, a transmission frequency of an RF magnetic field irradiated in accordance with the water signal suppression pulse sequence, a transmission frequency of an RF magnetic field for excitation and inversion under the MRS measurement sequence, and a received frequency at the detection of the magnetic resonance signal, upon the repetitive measurements.

Figure 9:
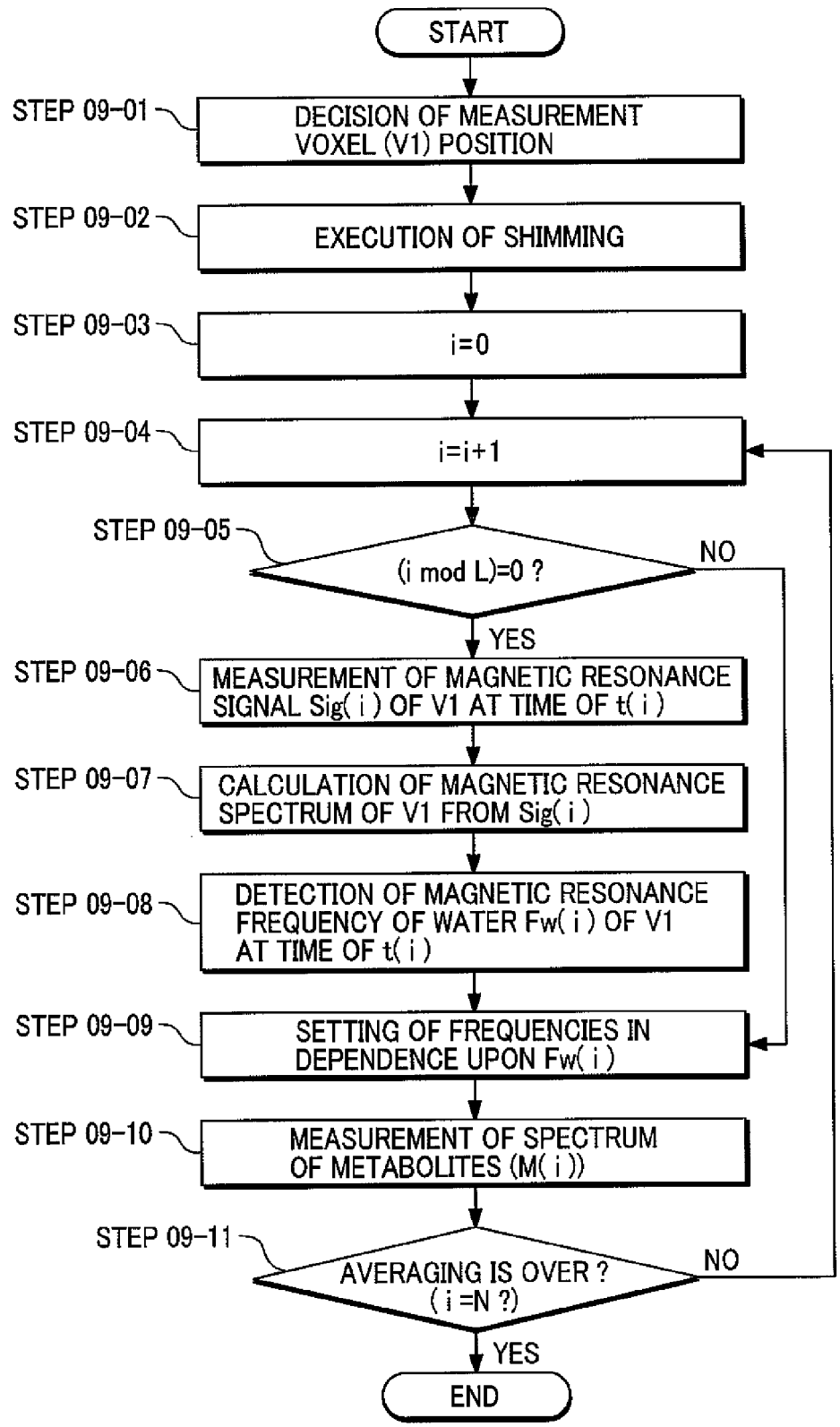
FIG. 9 is a flowchart showing a procedure for MRS measurement in an embodiment 2 of the present invention.

FIG. 9 is a flowchart showing a procedure for MRS measurement, which is employed in the embodiment 2 of the present invention. A specific imaging procedure will be explained below.

STEP09-01: An imaging voxel V1 of a target is determined.

STEP09-02: Shimming for enhancing the uniformity of a static magnetic field is performed if necessary.

STEPS09-04 and -05: In order to detect water magnetic resonant frequencies every L times, a decision is made as to whether the remainder (i mod L) obtained by dividing the number of measurements (where i=1, 2, 3, . . . , N) by L is 0.

(STEP09-06): A first magnetic resonance signal Sig (1) generated from the imaging voxel V1 is acquired at a first time t(1) using the MRS pulse sequence shown in FIG. 3 as a first pre-scan.

STEP09-07: Fourier transform is effected on Sig (1) to calculate a first magnetic resonance spectrum.

STEP09-08: A first water magnetic resonant frequency Fw1 is detected from the first magnetic resonance spectrum.

STEP09-09: Next, when a magnetic resonance signal measurement (corresponding to such a measurement that the pulse sequence shown in FIG. 4, for suppressing the water signal and the MRS pulse sequence shown in FIG. 3 are continuously conducted) accompanied with N-time repetitive measurements is executed after the time t(1), set values of a transmission frequency Fwt(i) of an RF magnetic field irradiated to suppress a water signal set by each repeated measurement M(i) (where i=1, 2, 3, . . . , L), a transmission frequency Ft(i) of an RF magnetic field irradiated to select and excite the imaging voxel V1, and a received frequency Fr(i) at the detection of a magnetic resonance signal generated from the imaging voxel V1 are respectively calculated in accordance with the following equations (5), (6) and (7) on the basis of the water magnetic resonant frequency Fw1 upon measurements up to a predetermined number of times L:

$$Fwt(i)=Fw1 \tag{5}$$

$$Ft(i)=Fw1 \tag{6}$$

$$Fr(i)=Fw1 \tag{7}$$

STEP09-10: Next, the pulse sequence shown in FIG. 4, for suppressing the water signal and the MRS pulse sequence shown in FIG. 3 are continuously performed using the set values (Fwt(i), Ft(i) and Fr(i)) to thereby carry out a spectrum measurement M(i) of metabolites. The spectrum measurement is repeated L times (M(i) (where i=1, 2, 3, . . . , L). After the completion of the measurements of the predetermined number of times corresponding to the Lth time, measurement similar to STEP09-06 and processes similar to STEPS09-07 and 08 are repeatedly performed again to thereby detect a second water magnetic resonant frequency Fw2 at a second time t(2). Further, a process similar to STEP09-09 and measurement similar to STEP09-10 are repeated to carry out measurements M(i) (where i=(L+1), 2, 3, . . . , 2L). Thus, the water magnetic resonant frequencies are re-detected every L times, and repetitive measurements of N times are performed (Step09-11) while the setting (correction) of each frequency is being performed, whereby a high-precision MRS measurement is enabled even in circumstances when a change in magnetic resonant frequency with a variation in magnetic field during measurement or the like exists.

Figure 10A:
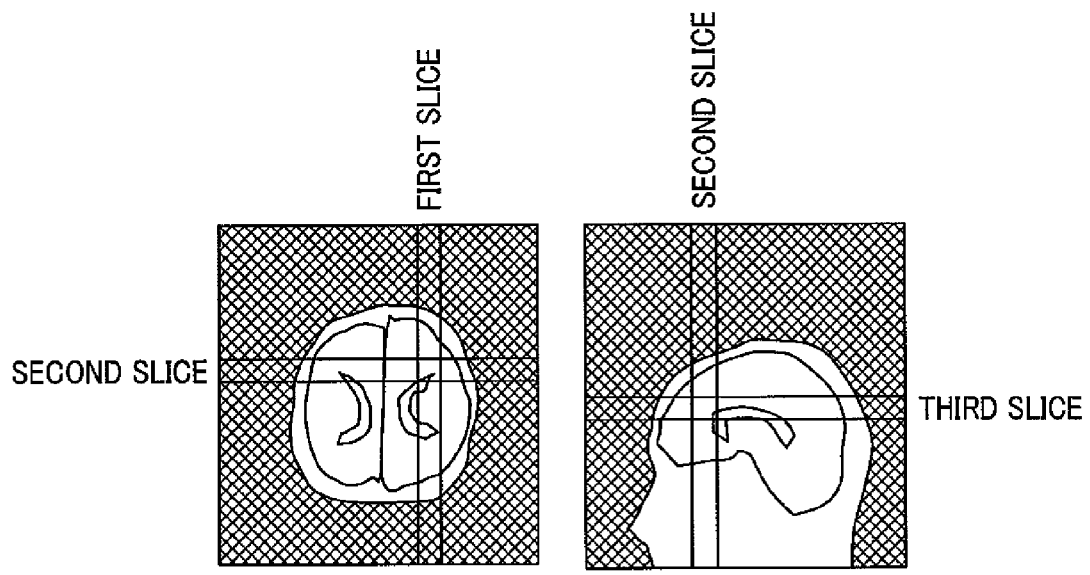
FIG. 10A is a view showing the positions of imaging voxels.
Figure 10B:
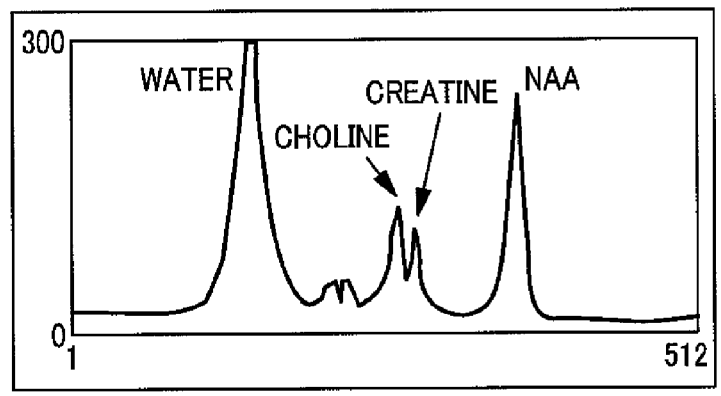
FIG. 10B is a view illustrating an example of a measurement result of MRS, which is measured in accordance with the flowchart of FIG. 9 where no time continuity occurs in a variation characteristic of a static magnetic field.

FIG. 10 is a measurement result example at the time that the measurement is conducted in accordance with the procedure of FIG. 9 where no time continuity exists in a varying rate of a static magnetic field strength. FIG. 10A shows the positions of imaging voxels determined on magnetic resonance images, and FIG. 10B shows a spectrum obtained from the imaging voxels. In FIG. 10B as compared with FIG. 6B, a water signal is sufficiently suppressed and a half-value width of a peak of NAA is also made narrow. The peaks of choline and creatine can also be separated.

Although the embodiment 2 has described the case in which upon spectrum measurements of L times subsequent to the detection of each water magnetic resonant frequency, the various frequency settings are conducted with the detected water magnetic resonant frequency itself as the reference, estimated processing similar to the method of the embodiment 1 is performed to estimate water magnetic resonant frequencies at respective measurement times during L times. Thereafter, various frequency settings may be conducted with each estimated value as the reference.

Since the pre-scan of the magnetic resonance signal for detecting the water magnetic resonant frequency is additionally conducted in addition to the pulse sequence shown in FIG. 4 for suppressing the water signal and the MRS pulse sequence shown in FIG. 3 in the embodiment 2, a total measurement time becomes long depending upon "the ratio of the number of pre-scans to the number of measurements shown in FIGS. 4 and 3". When it is known in advance that, for example, the frequency with which the magnetic resonant frequency changes instantaneously, is low, "the ratio of the number of pre-scans to the number of measurements in FIGS. 4 and 3" can be rendered small. Therefore, an increase in the measurement time may be small. When, however, the frequency with which the magnetic resonant frequency changes instantaneously is high or entirely unknown, it is necessary to increase "the ratio of the number of pre-scans to the number of measurements in FIGS. 4 and 3", and the measurement time greatly increases.

In order to avoid the increase in the measurement time, the excitation band widths of the first RF magnetic field RF1 and second RF magnetic field RF2 of FIG. 3 are rendered narrow when the pre-scan for detecting the water magnetic resonant frequency is performed using the MRS pulse sequence shown in FIG. 3. Upon the pre-scan, nuclear magnetization contained in water may be excited and the excitation of nuclear magnetization contained in metabolites may be avoided. If the excitation of the nuclear magnetization contained in the metabolites is avoided during the pre-scan, then longitudinal relaxation of the nuclear magnetization contained in the metabolites proceeds without any delay even during the pre-scan. Therefore, if the pre-scan is done in a spare time of a repetitive measurement time for MRS measurement, then the scan or measurement for continuously performing the pulse sequence shown in FIG. 4 for suppressing the water signal and the MRS pulse sequence shown in FIG. 3, and the pre-scan can be repeated without extending or prolonging the total measurement time (since the longitudinal relaxation time of metabolites is long upon MRS measurement, a long repetition time of two seconds or so is often set, and a spare time during which the application of an RF magnetic field and a gradient magnetic field and the detection of a magnetic resonance signal are not carried out, is normally often taken as one second or so). Incidentally, a SINC waveform or a Gauss waveform having an excitation frequency characteristic of a narrow bandwidth equivalent to a water signal peak width or so may be used to excite nuclear magnetization contained in water.

In order to avoid a large increase in the measurement time, the flip angle of the first RF magnetic field RF1 irradiated in accordance with the MRS pulse sequence may be set smaller than 90° upon execution of the pre-scan for detecting the water magnetic resonant frequency. If the nuclear magnetization contained in the metabolites is excited so as not to bring down so much during the pre-scan, it is then not necessary to take long time so much for sufficiently recovering the longitudinal magnetization of a nuclear spin contained in each metabolite. Therefore, if the pre-scan is done during the spare time of the repetitive measurement time for MRS measurement, then the scan or measurement for continuously performing the pulse sequence shown in FIG. 4 for suppressing the water signal and the MRS pulse sequence shown in FIG. 3, and the pre-scan can be repeated without extending or prolonging the total measurement time (since the longitudinal relaxation time of metabolites is long upon MRS measurement, a long repetition time of two seconds or so is often set, and a spare time during which the application of an RF magnetic field and a gradient magnetic field and the detection of a magnetic resonance signal are not carried out, is normally often taken as one second or so). Incidentally, since the nuclear magnetization contained in water is very large, then a water signal peak having a signal strength enough to detect a water magnetic resonant frequency can be generated even when the flip angle of RF1 is small.

In order to avoid the increase in the measurement time, a voxel V2 different from the imaging voxel V1 to be measured in MRS measurement may be set as a measurement voxel for a pre-scan done to detect a water magnetic resonant frequency when the pre-scan for detecting the water magnetic resonant frequency is performed using the MRS pulse sequence shown in FIG. 3 (if V2 is selected in the neighborhood of the imaging voxel V1, then time-varying rates of magnetic resonant frequencies at both voxels become equal). If the excitation of the imaging voxel V1 to be measured upon MRS measurement is avoided during the pre-scan, then longitudinal relaxation of nuclear magnetization contained in the imaging voxel V1 proceeds without any delay even during the pre-scan. Therefore, if the pre-scan is done in a spare time of a repetitive measurement time for MRS measurement, then the scan or measurement for continuously performing the pulse sequence shown in FIG. 4 for suppressing the water signal and the MRS pulse sequence shown in FIG. 3, and the pre-scan can be repeated without extending or prolonging the total measurement time (since the longitudinal relaxation time of metabolites is long upon MRS measurement, a long repetition time of two seconds or so is often set, and a spare time during which the application of an RF magnetic field and a gradient magnetic field and the detection of a magnetic resonance signal are not carried out, is normally often taken as one second or so).

Incidentally, when the voxel V2 to be measured upon the pre-scan is selected and excited, it is necessary to select and excite orthogonal three slices different from orthogonal three slices containing the imaging voxel V1 to be measured upon the MRS measurement. As specific changes in the MRS sequence, the respective transmission frequencies of the first RF magnetic field RF1, second RF magnetic field RF2 and third RF magnetic field RF3 may be changed without changing the slice selecting gradient magnetic fields Gs1, Gs2 and Gs3 shown in FIG. 3 (orthogonal three slices placed in positions away respective slice widths or more from one another).

In order to avoid the large increase in the measurement time, the pre-scan may be performed only when the magnetic resonant frequency is shift, without always performing the pre-scan for detecting the water magnetic resonant frequency for each predetermined number of times as in the case of the measurement procedure shown in FIG. 9. In order to make a decision as to whether the magnetic resonant frequency is shifted, a change in water signal peak strength (peak area) of each spectrum obtained by the scan or measurement for continuously performing the pulse sequence shown in FIG. 4 for suppressing the water signal and the MRS pulse sequence shown in FIG. 3 is monitored. When the magnetic resonant frequency is shifted and the water signal peak strength (peak area) is increased to a predetermined value or more, the magnetic resonant frequency is judged to have been shifted, and the pre-scan may be carried out. Incidentally, the absolute value of the water signal peak strength (peak area) may be specified as the predetermined value. Alternatively, an absolute value relative to a water signal peak strength (peak area) of a spectrum obtained by a first or previous measurement may be used.

Although each of the embodiments 1 and 2 has explained the example in which the received frequency at the detection of the magnetic resonance signal is corrected, an advantageous effect similar to the case where the received frequency is corrected can be obtained by subsequent processing without correcting the received frequency during measurement if individual spectrum data prior to being subjected to averaging are all saved. That is, if a peak position of a residual-water signal or a peak position of a metabolite signal is detected with respect to each individual spectrum data prior to being subjected to averaging, and such subsequent processing that the peak position of the residual-water signal or the peak position of the metabolite signal becomes the same, is effected on all spectrum data and thereafter averaging processing is performed, then a sufficient addition effect can be obtained. Incidentally, since the strength of the metabolite signal at each individual spectrum is very small, continuous spectrum data corresponding to several times as viewed back and forth are added together and thereafter the peak position of the metabolite signal may be detected.

Although each of the embodiments 1 and 2 has taken the pulse sequence of FIG. 3 by way of example as the MRS sequence, a similar effect can be obtained even in the case of an MRS sequence other than FIG. 3.

FIG. 11 is a view showing an example of another MRS pulse sequence applicable to the embodiment of the present invention. In FIG. 11, TR indicates a repetition time, TE indicates an echo timer and TM is a time indicative of an irradiation interval of each of a second RF magnetic field pulse RF2 and a third RF magnetic field pulse RF3. In the pulse sequence shown in FIG. 11, a first gradient magnetic field (gradient magnetic field in an X-axis direction) Gs1 for selection of a first slice (plane orthogonal to an X axis), and a first RF magnetic field RF1 called "90° pulse" are first applied simultaneously to bring nuclear magnetization in the first slice into an excitation state.

After the elapse of TE/2 from the irradiation of RF1, a second gradient magnetic field (gradient magnetic field in a Y-axis direction) Gs2 for selection of a second slice (plane orthogonal to a Y axis), and a second RF magnetic field RF2 called "90° pulse" are simultaneously applied to thereby enable nuclear magnetization contained even in the second slice, of the nuclear magnetization in the first slice excited by RF1 to be 90° rotated.

After the elapse of TM from the irradiation of RF2, a third gradient magnetic field (gradient magnetic field in a Z-axis direction) Gs3 for selection of a third slice (plane vertical to a Z axis), and a third RF magnetic field RF3 called "90° pulse" are simultaneously applied to thereby enable nuclear magnetization contained even in the third slice, of the nuclear magnetization lying in an intersection area of the first slice and the second slice rotated by RF2 to be 90° rotated again.

With the application of the above three sets of RF magnetic fields and gradient magnetic fields, a magnetic resonance signal Sig1 with the point of time subsequent to TE/2 from the irradiation of RF3 as an echo time is generated.

Incidentally, Gs1' applied immediately after the application of Gs1, Gs2' applied immediately after the application of Gs2, and Gs3' applied immediately after the application of Gs3 are respectively gradient magnetic fields for rephase with respect to Gs1, Gs2 and Gs3.

By executing the pulse sequence shown in FIG. 11, only nuclear magnetization contained in an area (imaging voxel) V1 at which the three of the first, second and third slices intersect, can selectively be excited. Then, a magnetic resonance signal generated from the imaging voxel V1 is measured and Fourier transform is effected on the measured magnetic resonance signal, whereby a magnetic resonance spectrum of the imaging voxel V1 can be obtained.

The above description has been made of the case in which the present invention is applied to the MRS measurement. However, a high-precision MRSI measurement can be carried out by correcting a magnetic resonant frequency under MRSI measurement in accordance with a method similar to the method referred to above. Incidentally, since measurement repetition is conducted even for phase-encoding upon the MRSI measurement in addition to measurement repetition for averaging, a similar precision enhancing effect can be obtained by effecting a procedure similar to the frequency correcting method with respect to "the change in frequency between the repetitive measurements for averaging" described in FIGS. 7 and 8, even on "the change in frequency between the repetitive measurements for phase encode". By correcting the transmission frequency of the RF magnetic field irradiated in accordance with the water signal suppression sequence using the present invention particularly when the water signal suppression sequence shown in FIG. 4 and the MRSI sequence are executed continuously, a sufficient water suppression effect can be obtained even where the repetition of the phase encode and the repetition of averaging are conducted.

In the case of a series of continuous measurements in which an ultrahigh-speed imaging sequence called echo planar imaging is done repeatedly, a position displacement of each imaging slice and a position displacement in a phase-encoding direction take place when a change in magnetic resonant frequency occurs during measurement. Therefore, in a functional MRI or the like using information on the difference between echo planar images, a method similar to that at the above-described spectrum measurement is used for a transmission frequency of an RF magnetic field for area selective excitation or/and a received frequency of a magnetic resonance signal, thereby making it possible to reduce the position displacement of each imaging slice or/and the position displacement in the phase-encoding direction.

Using a method similar to that at the abovementioned spectrum measurement, a frequency correction is effected on an imaging sequence (angiography or the like) long in measurement time, or an imaging sequence (temperature measurement or the like) using phase information of a magnetic resonance signal, thereby making it possible to reduce a position displacement and a shift in phase information.

INDUSTRIAL APPLICABILITY

According to the present invention, a magnetic resonance imaging system can be provided which is capable of performing a high-precision spectrum measurement even when a magnetic resonant frequency changes during measurement.

What is claimed is:

1. A magnetic resonance imaging system comprising:
means for generating a static magnetic field;
gradient magnetic field generating means for generating a gradient magnetic field;
RF magnetic field generating means for generating an RF magnetic field;
measuring means for measuring a magnetic resonance signal generated from a target; and
sequence control means configured to set operating conditions to respective portions of the gradient magnetic field generating means, the RF magnetic field generating means and measuring means;
said sequence control means being configured to:
 (1) execute a water suppression sequence for applying the RF magnetic field and the gradient magnetic field to the target to thereby suppress a signal of water;
 (2) determine that a magnetic resonant frequency of water has been shifted when the calculated signal strength of water signal peak is increased to a predetermined value or more, and
 (3) set a transmission frequency of the RF magnetic field irradiated and/or set a received frequency at the detection of the magnetic resonance signal.

* * * * *